US012582807B2

(12) United States Patent
Wada et al.

(10) Patent No.: US 12,582,807 B2
(45) Date of Patent: Mar. 24, 2026

(54) VALVE BODY AND MEDICAL INSTRUMENT PROVIDED WITH VALVE BODY

(71) Applicant: TERUMO KABUSHIKI KAISHA, Tokyo (JP)

(72) Inventors: Satoshi Wada, Shizuoka (JP); Katsuaki Soma, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 861 days.

(21) Appl. No.: 17/826,524

(22) Filed: May 27, 2022

(65) Prior Publication Data

US 2022/0280757 A1 Sep. 8, 2022

Related U.S. Application Data

(63) Continuation of application No. PCT/JP2020/044245, filed on Nov. 27, 2020.

(30) Foreign Application Priority Data

Nov. 29, 2019 (JP) ................................. 2019-217241

(51) Int. Cl.
*A61M 25/06* (2006.01)
*A61M 29/02* (2006.01)
*A61M 39/06* (2006.01)

(52) U.S. Cl.
CPC ........ *A61M 25/0662* (2013.01); *A61M 29/02* (2013.01); *A61M 39/0693* (2013.01); *A61M 2039/062* (2013.01); *A61M 2039/068* (2013.01)

(58) Field of Classification Search
CPC .......... A61M 39/045; A61M 2039/064; A61M 2039/0673; A61M 2039/068;

(Continued)

(56) References Cited

U.S. PATENT DOCUMENTS

| | | | | |
|---|---|---|---|---|
| 5,350,363 A | * | 9/1994 | Goode | .............. A61M 39/0606 |
| | | | | 604/167.04 |
| 5,538,505 A | * | 7/1996 | Weinstein | ......... A61M 39/0606 |
| | | | | 604/167.04 |

(Continued)

FOREIGN PATENT DOCUMENTS

| | | |
|---|---|---|
| JP | 2011212417 A | 10/2011 |
| JP | 2016512755 A | 5/2016 |

(Continued)

OTHER PUBLICATIONS

English Translations of the International Search Report (Form PCT/ISA/210) and the Written Opinion of the International Searching Authority (Form PCT/ISA/237) issued Feb. 2, 2021, by the Japanese Patent Office in corresponding International Application No. PCT/JP2020/044245. (6 pages).

(Continued)

*Primary Examiner* — Kami A Bosworth
(74) *Attorney, Agent, or Firm* — BUCHANAN INGERSOLL & ROONEY PC

(57) ABSTRACT

A valve body and a medical instrument provided with the valve body can stably maintain sealing performance for preventing air/blood leakage while maintaining a smooth insertion feeling even when various types of medical devices are repeatedly inserted and removed. The valve body includes a main body portion having oppositely facing first and second surfaces, an outer peripheral surface extending between the first and second surfaces, and an insertion portion having an inner surface defining a gap that allows insertion of a medical device and formed at least on the first surface. The main body portion contains a self-repairing material that allows self-repairing damage resulting from contact with the medical device. At least part of the inner surface of the insertion portion is provided with a coating (Continued)

layer that prevents the gap from being closed by self-repair when portions of the inner surface of the insertion portion contact each other.

20 Claims, 8 Drawing Sheets

(58) Field of Classification Search
CPC .. A61M 2039/0686; A61M 2039/2426; A61M 39/04; A61M 2039/042; A61M 2039/047
See application file for complete search history.

(56) References Cited

U.S. PATENT DOCUMENTS

| | | | | | |
|---|---|---|---|---|---|
| 5,738,664 | A | * | 4/1998 | Erskine | A61M 39/04 604/256 |
| 2010/0179480 | A1 | * | 7/2010 | Sugiki | F16K 15/147 604/167.04 |

| | | | | | |
|---|---|---|---|---|---|
| 2012/0116493 | A1 | | 5/2012 | Harada | |
| 2012/0157924 | A1 | | 6/2012 | Schutz et al. | |
| 2013/0046241 | A1 | | 2/2013 | Okamura et al. | |
| 2014/0276498 | A1 | | 9/2014 | Connor et al. | |
| 2016/0331935 | A1 | | 11/2016 | Saatchi et al. | |
| 2017/0233533 | A1 | | 8/2017 | Harada | |
| 2018/0142787 | A1 | * | 5/2018 | Herzog | F16J 15/022 |
| 2021/0154361 | A1 | * | 5/2021 | Busam | A61M 39/06 |

FOREIGN PATENT DOCUMENTS

| | | | |
|---|---|---|---|
| WO | 2011016386 | A1 | 2/2011 |
| WO | 2016006413 | A1 | 1/2016 |

OTHER PUBLICATIONS

International Search Report (PCT/ISA/210) with translation and Written Opinion (PCT/ISA/237) mailed on Feb. 2, 2021, by the Japan Patent Office as the International Searching Authority for International Application No. PCT/JP2020/044245. (9 pages).

* cited by examiner

VALVE BODY AND MEDICAL INSTRUMENT PROVIDED WITH VALVE BODY

CROSS-REFERENCES TO RELATED APPLICATIONS

This application is a continuation of International Patent Application No. PCT/JP2020/044245 filed on Nov. 27, 2020, which claims priority to Japanese Patent Application No. 2019-217241 filed on Nov. 29, 2019, the entire content of both of which is incorporated herein by reference.

TECHNOLOGICAL FIELD

The present invention relates to a valve body and a medical instrument provided with the valve body. The medical instrument provided with the valve body is, for example, a sheath introducer, an introducer, and a connector member.

BACKGROUND DISCUSSION

In a catheter procedure, various devices are introduced into a blood vessel through a valve body (hemostatic valve) disposed on a hub of a sheath introducer or a valve body (hemostatic valve) disposed on a hub of a connector member attached to a proximal end of a catheter. The sheath introducer is required to prevent air inflow into the sheath introducer and to reduce blood leakage from a proximal end of the sheath introducer. The connector member is required to, when introducing the various devices into the blood vessel through a valveless catheter such as a guiding catheter, be connected to the proximal end of the catheter to prevent the air inflow into the catheter and reduce the blood leakage from the proximal end of the catheter. Therefore, various valve bodies are used for the sheath introducer and the connector member in order to prevent air embolization. For example, United States Patent Application Publication No. 2016/0331935 discloses a valve body formed with a slit having a function as an insertion portion for introducing a medical elongated body such as a catheter device or a guide wire into the valve body.

In recent years, a catheter procedure is used for diagnosis and treatment of various lesion sites. In treatment for a complicated lesion site, a surgeon inserts a plurality of types of medical elongated bodies having different product specifications, such as different outer diameters, into a blood vessel through a sheath introducer or a connector member, and operates these medical elongated bodies to treat the lesion site. During the catheter procedure, when inserting a dilator into the sheath introducer and when inserting a catheter device through the sheath introducer or the connector member, the surgeon needs to aim at a central portion of the valve body and guide the medical elongated body in order to prevent the valve body from being damaged. Accordingly, the operation for the sheath introducer or the connector member during the catheter procedure is complicated, which may prolong the catheter procedure time. Hereinafter, in the present specification, the catheter device, the guide wire, the dilator, and the like, which are introduced into a living body through the sheath introducer or the connector member, are collectively referred to as the "medical elongated body" or "elongated medical body".

When the valve body of the sheath introducer or connector member is damaged during the catheter procedure, the sheath introducer or connector member needs to be replaced, and medical economics are impaired, such as a cost of a new sheath introducer or connector member, and a time loss associated with insertion of the new sheath introducer or attachment of the new connector member. Therefore, the valve body is required to be capable of maintaining sealing performance even in a severe catheter operation while maintaining ease of the insertion when inserting the medical elongated body.

SUMMARY

Disclosed here is a valve body and a medical instrument provided with the valve body that are capable of stably maintaining sealing performance for preventing air or blood leakage while maintaining a smooth insertion feeling even when various types of medical elongated bodies are repeatedly inserted and removed.

According to one aspect of the disclosure, a valve body includes a main body portion. The main body portion includes a first surface, a second surface facing away from the first surface, an outer peripheral surface extending between the first surface and the second surface, and an insertion portion having an inner surface defining a gap that allows insertion of a medical elongated body and formed at least on the first surface. The main body portion contains a self-repairing material that allows self-repairing damage formed by contact with the medical elongated body. At least a part of the inner surface of the insertion portion is provided with a coating layer that prevents the gap from being closed by self-repair in a state in which portions of the inner surface of the insertion portion are in contact with each other.

In the valve body according to the disclosure here, since the main body portion of the valve body contains the self-repairing material, even when the damage occurs in the valve body when an operation of inserting the medical elongated body through the gap formed in the valve body is repeated a plurality of times, the damage of the valve body can be repaired by the self-repairing material. Therefore, the valve body can maintain sealing performance of the valve body. In the valve body disclosed here, since the inner surface of the insertion portion defining the gap is provided with the coating layer that prevents the portions of the inner surface from connecting by self-repair, even in a state in which the portions of the inner surface of the insertion portion are in contact with each other, the gap can be prevented from being closed by the self-repairing material. Therefore, the valve body allows a surgeon to easily grasp a position of the insertion portion of the valve body based on the gap formed in the valve body, and can prevent an increase in insertion resistance when the surgeon inserts the medical elongated body into the valve body.

Another aspect of the disclosure involves a sheath introducer configured to allow an elongated medical body to be introduced into a blood vessel. The sheath introducer comprises: a tubular member including a lumen through which the elongated medical body is insertable; a hub connected to the proximal end of the tubular member and including an internal space in communication with the lumen of the tubular member; a valve body positioned in the internal space of the hub; and a cap member abutting against the valve body to fix the valve body in the internal space of the hub, with the cap member including a through hole through which the elongated medical body is insertable. The valve body positioned in the internal space of the hub is compressed by the cap member in a direction causing portions of the inner surface of the insertion portion that face one another in the gap to contact each other. The valve body comprises: a main body portion that includes oppositely facing first and second surfaces, and an outer peripheral surface extending between the first surface and the second surface; an insertion portion having an inner surface defining a gap that allows insertion of the elongated medical body, with the insertion portion being formed at least on the first surface. The main body portion contains a self-repairing material that allows self-repairing damage of the main body formed by contact with the elongated medical body, and at least a part of the inner surface of the insertion portion is provided with a coating layer that prevents the gap from being closed by self-repair when the portions of the inner surface of the insertion portion that face one another in the gap are in contact with each other.

A further aspect of the disclosure involves an introducer comprising: a sheath introducer and a dilator. The sheath introducer includes a sheath introducer to allow an elongated medical body to be introduced into a blood vessel, wherein the sheath introducer comprises: a tubular member including a lumen through which the elongated medical body is insertable; a hub connected to the proximal end of the tubular member and including an internal space in communication with the lumen of the tubular member; a valve body positioned in the internal space of the hub; and a cap member abutting against the valve body to fix the valve body in the internal space of the hub, wherein the cap member includes a through hole through which the elongated medical body is insertable. The valve body in the internal space of the hub is compressed by the cap member in a direction causing portions of the inner surface of the insertion portion that face one another in the gap to contact each other. The valve body comprises: a main body portion that includes oppositely facing first and second surfaces, and an outer peripheral surface extending between the first surface and the second surface; an insertion portion having an inner surface defining a gap that allows insertion of the elongated medical body, with the insertion portion formed at least on the first surface. The main body portion contains a self-repairing material that allows self-repairing damage of the main body formed by contact with the elongated medical body, and at least a part of the inner surface of the insertion portion is provided with a coating layer that prevents the gap from being closed by self-repair when the portions of the inner surface of the insertion portion that face one another in the gap are in contact with each other. The dilator comprises a dilator main body insertable into the lumen of the tubular member of the sheath introducer through the through hole of the cap member, and a dilator hub fixed to the proximal end of the dilator main body. The thickness of the main body portion of the valve body being smaller than the outer diameter of the maximum outer diameter portion of the dilator main body.

BRIEF DESCRIPTION OF THE DRAWINGS

FIG. 9 is an exploded perspective view of a valve body according to a first modification.

FIG. 10 is a cross-sectional view of a valve body according to a second modification.

DETAILED DESCRIPTION

Hereinafter, an introducer 10, a sheath introducer 100, and a valve body 110 according to an embodiment, and representing examples of the new introducer, sheath introducer and valve body disclosed here, will be described with reference to FIGS. 1 to 8.

Figure 1:
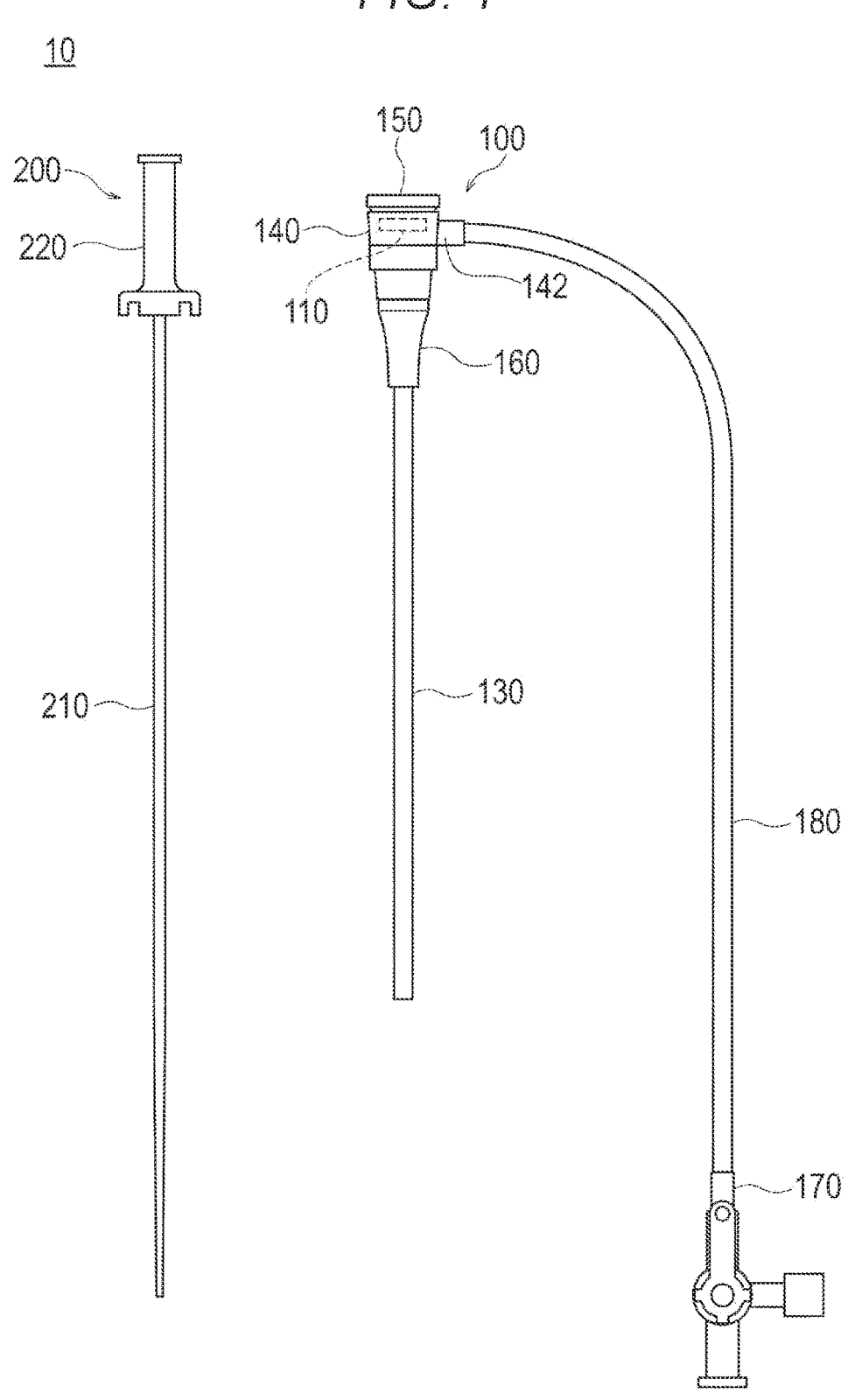
FIG. 1 is a view illustrating an introducer according to an embodiment.
Figure 2:
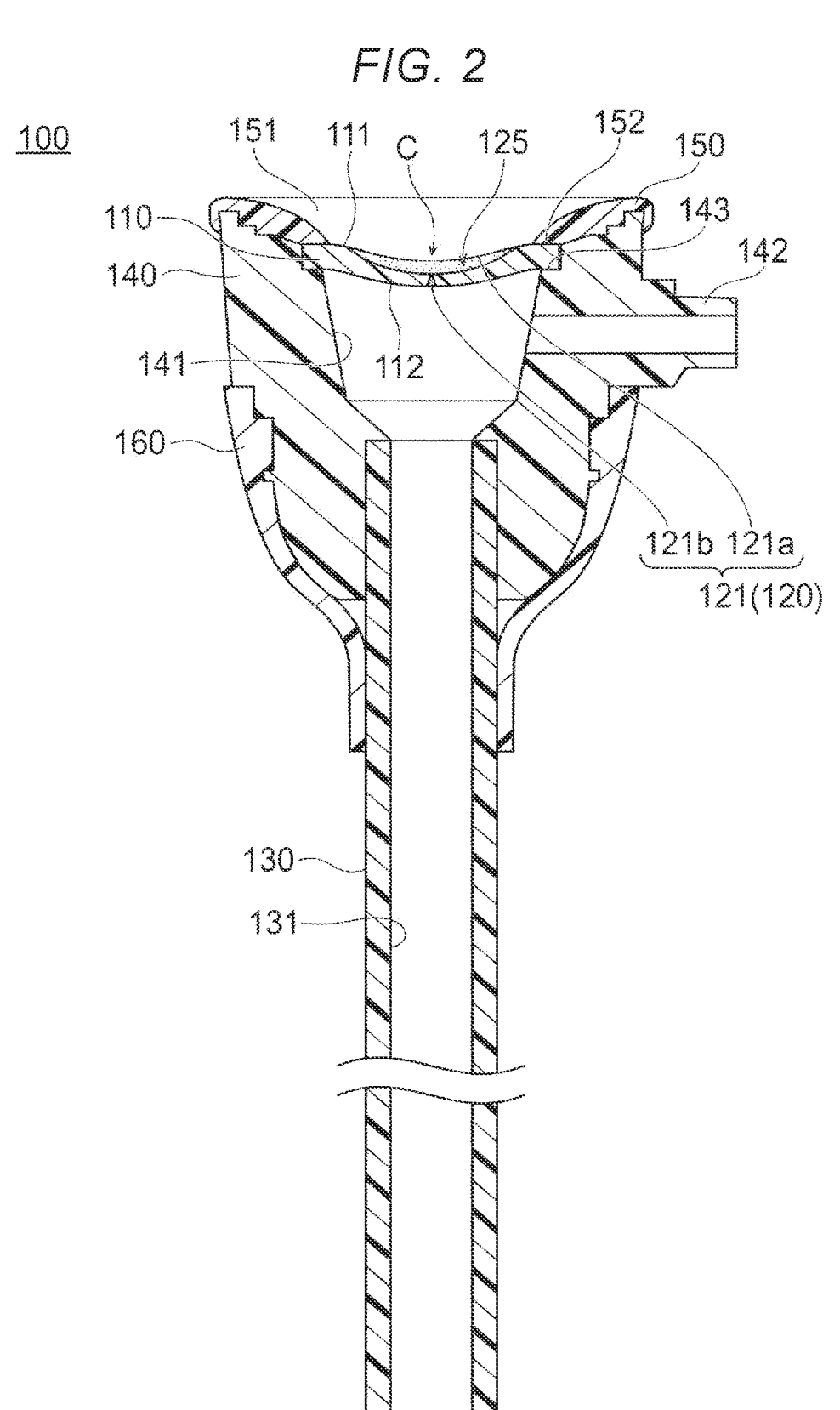
FIG. 2 is a cross-sectional view of a sheath introducer according to the embodiment.
Figure 3:
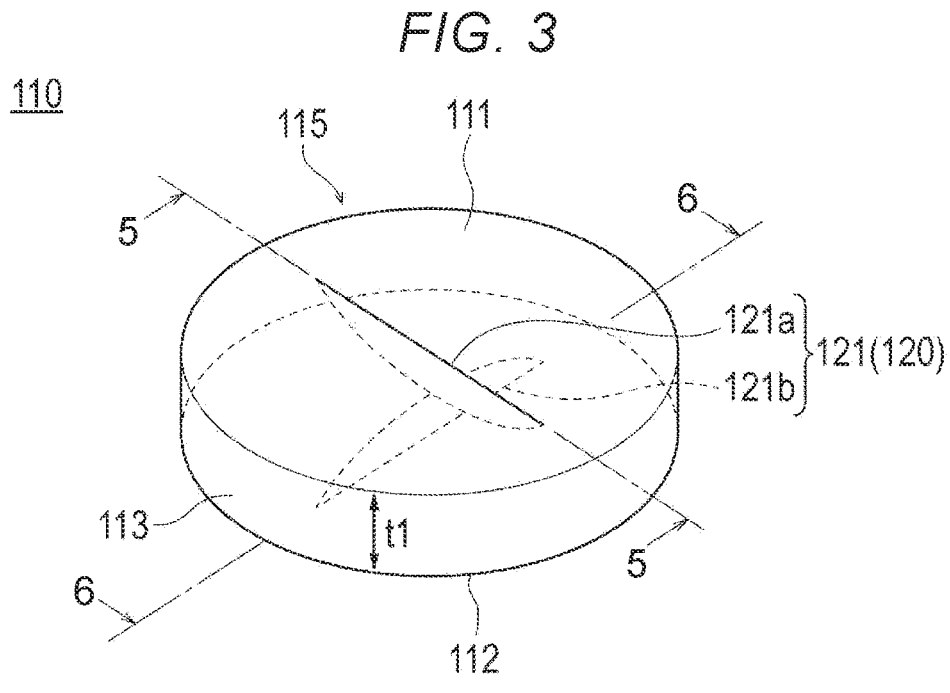
FIG. 3 is a perspective view of a valve body according to the embodiment.
Figure 4:
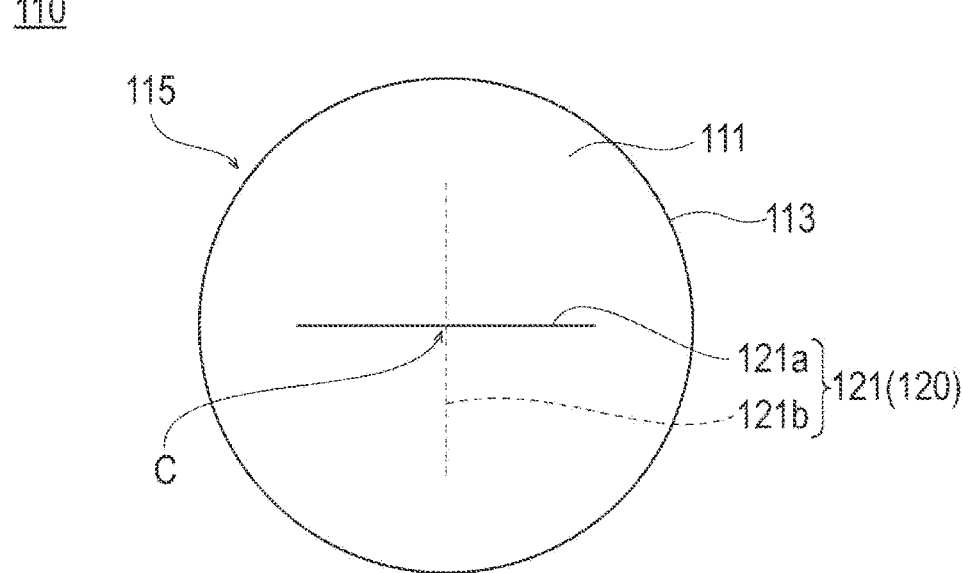
FIG. 4 is a top view of the valve body according to the embodiment.
Figure 5:
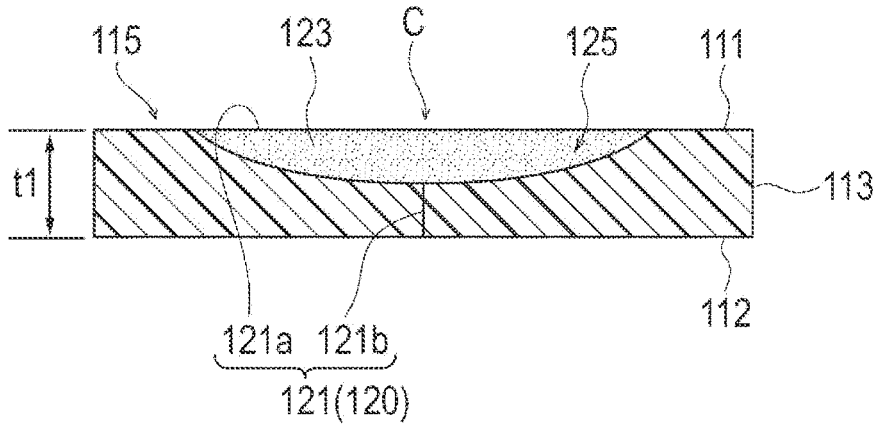
FIG. 5 is a cross-sectional view of the valve body taken along a line 5-5 illustrated in FIG. 3.
Figure 6:
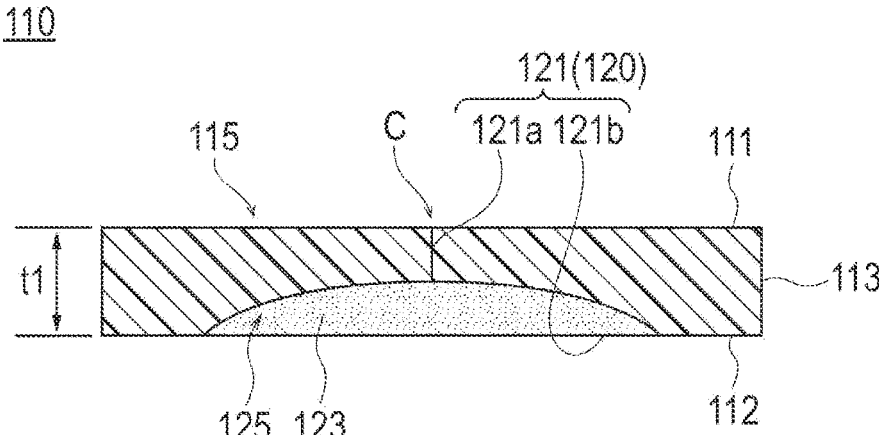
FIG. 6 is a cross-sectional view of the valve body taken along a line 6-6 illustrated in FIG. 3.
Figure 7:
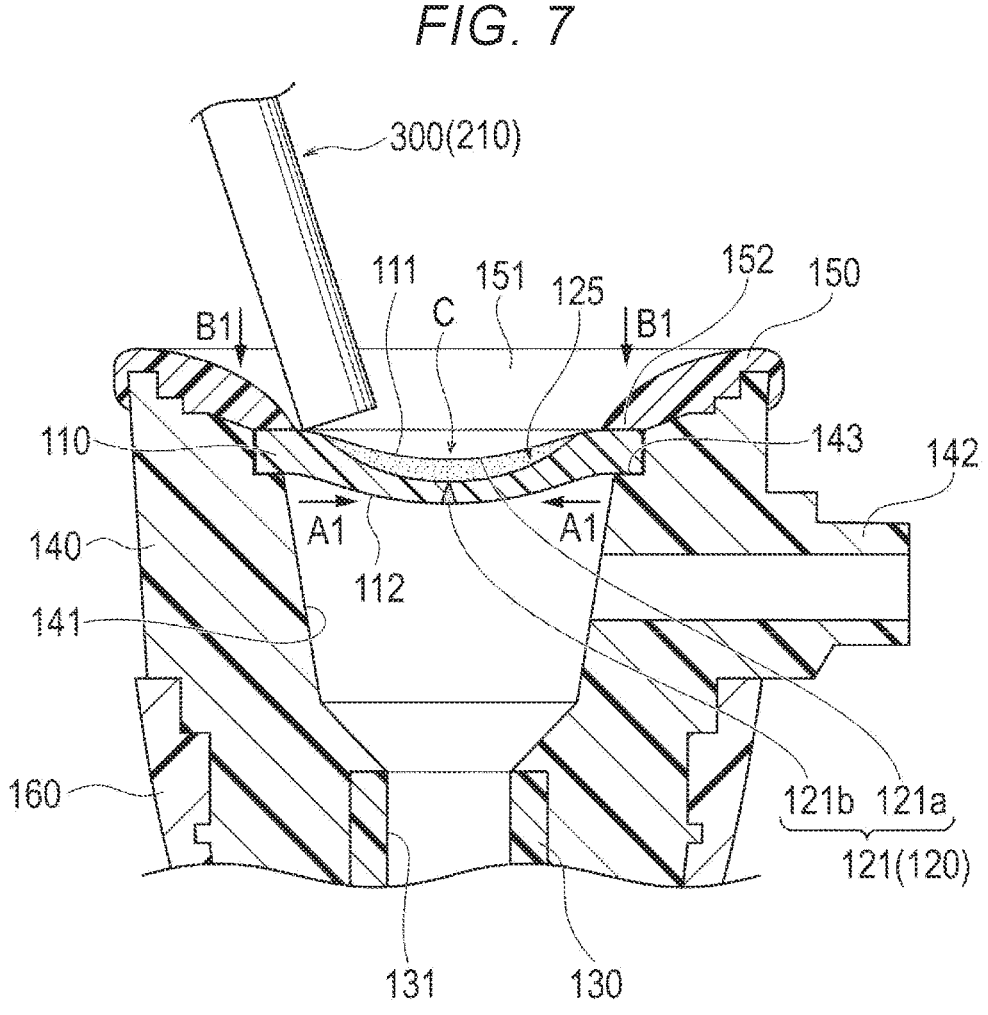
FIG. 7 is a cross-sectional view illustrating a use example of the sheath introducer according to the embodiment.
Figure 8:
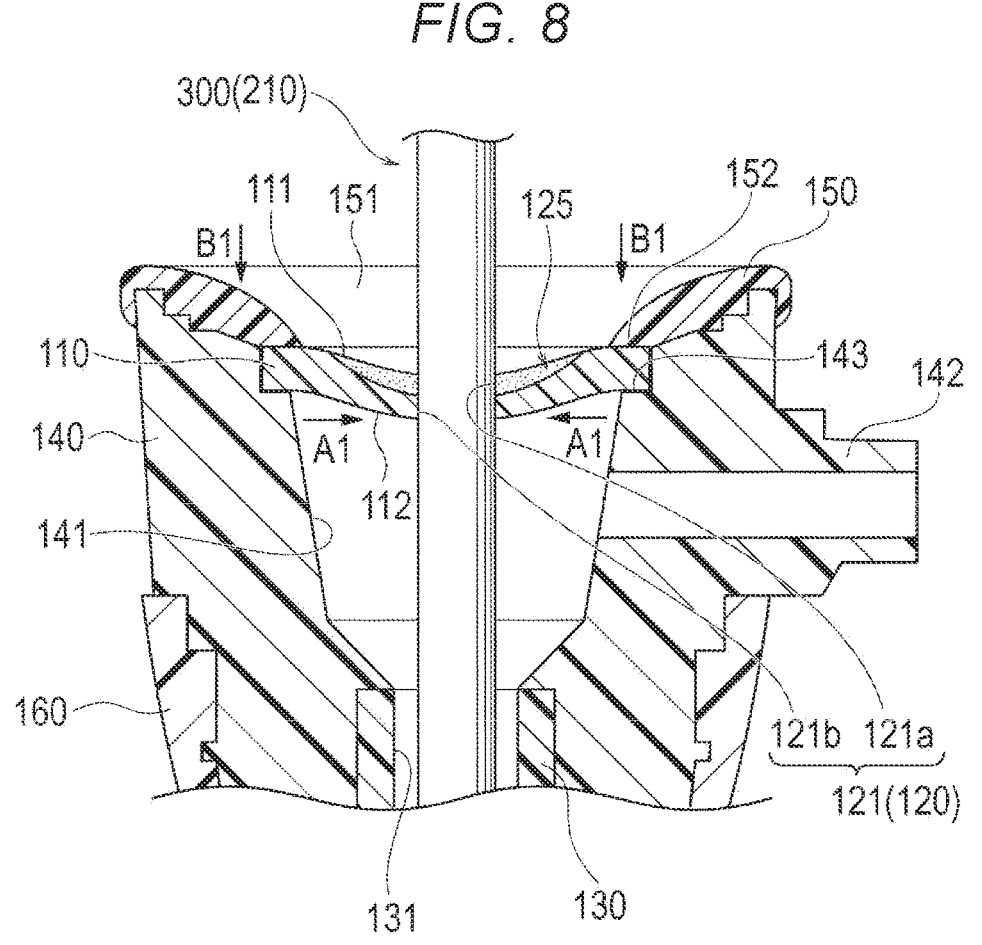
FIG. 8 is a cross-sectional view illustrating a use example of the sheath introducer according to the embodiment.

FIG. 1 illustrates a simplified overall configuration of the introducer 10. FIG. 2 illustrates a cross section of the sheath introducer 100 along an axial direction, FIGS. 3 and 4 illustrate the valve body 110, FIGS. 5 and 6 illustrate cross-sectional views of the valve body 110, and FIGS. 7 and 8 illustrate use examples of the sheath introducer 100.

In the present specification, a side on which a hub 140 is disposed (an upper side in FIG. 1) in the sheath introducer 100 is referred to as a proximal side (proximal end). In the sheath introducer 100, a side opposite to the proximal side and on which the sheath introducer 100 is introduced into a living body (a lower side in FIG. 1) is referred to as a distal side (distal end). A direction in which a tubular member 130 of the sheath introducer 100 extends (a vertical direction in FIG. 1) is referred to as the axial direction.

As illustrated in FIG. 1, the introducer 10 includes the sheath introducer 100 and a dilator 200.

The sheath introducer 100 can be used to introduce a medical elongated body 300 (see FIG. 8) such as a catheter device, a guide wire, and a dilator main body 210 of the dilator 200 into a blood vessel through a lumen 131 of the tubular member 130.

Valve Body 110

As illustrated in FIG. 2, the valve body 110 according to the present embodiment can be disposed in an internal space 141 of the hub 140 of the sheath introducer 100.

The valve body 110 has a function of preventing air from flowing into the lumen 131 of the tubular member 130 from outside, and a function of preventing blood flowing into the lumen 131 of the tubular member 130 from leaking to the outside.

Generally, as illustrated in FIGS. 3, 4, 5, and 6, the valve body 110 includes a main body portion 115 including a first surface 111, a second surface 112 facing away from the first surface 111, an outer peripheral surface 113 extending between the first surface 111 and the second surface 112, and an insertion portion 120 having an inner surface 123 defining a gap 121 that allows insertion of the medical elongated body 300 (see FIG. 8). The insertion portion 120 is formed at least on the first surface 111. The main body portion 115 contains a self-repairing material that allows self-repairing damage formed by contact with the medical elongated body 300. At least a part of the inner surface 123 of the insertion portion 120 is provided with a coating layer 125 that prevents the gap 121 from being closed by self-repair in a state in which portions of the inner surface 123 of the insertion portion 120 are in contact with each other.

The valve body 110 is formed in a substantially circular film shape (disc shape). As illustrated in FIG. 2, the valve body 110 is fixed to the internal space 141 of the hub 140 by a cap member 150 fitted to the hub 140. A shape of the valve body 110 is not particularly limited as long as the valve body 110 can be disposed in the internal space 141 of the hub 140.

As illustrated in FIGS. 3, 5, and 6, the gap 121 may be implemented by, for example, a slit formed in the main body portion 115. The inner surface 123 of the insertion portion 120 is thus constituted by surfaces or surface portions on either side of the slit that face one another.

The slit constituting the gap 121 includes a first slit portion 121a extending from the first surface 111 in a thickness direction (a vertical direction in FIGS. 5 and 6) of the main body portion 115, and a second slit portion 121b extending from the second surface 112 in the thickness direction of the main body portion 115. As illustrated in FIGS. 5 and 6, the first slit portion 121a and the second slit portion 121b intersect inside the main body portion 115. As shown in FIG. 3, the first slit portion 121a extends from the first surface 111 of the main body portion 115 toward the second surface 112 of the main body portion 115, and the first slit portion 121a may terminate in the thickness direction of the main body portion at a position spaced from the second surface 112 of the main body portion 115. Similarly, the second slit portion 121b extends from the second surface 112 of the main body portion 115 toward the first surface 111 of the main body portion 115, and the second slit portion 121b may terminate in the thickness direction of the main body portion 115 at a position spaced from the first surface 111 of the main body portion 115. The coating layer 125 may be provided on at least a part of the inner surface 123 defining the first slit portion 121a.

As illustrated in FIG. 5, the first slit portion 121a has an arc shape that is convexly curved from the first surface 111 toward the center of the main body portion 115 in the thickness direction. The second slit portion 121b has an arc shape that is convexly curved from the second surface 112 toward the center of the main body portion 115 in the thickness direction.

As illustrated in FIGS. 5 and 6, a bottom portion of the first slit portion 121a located substantially at the center of the main body portion 115 in the thickness direction overlaps an upper end portion of the second slit portion 121b located substantially at the center of the main body portion 115 in the thickness direction. As illustrated in FIG. 4, the first slit portion 121a and the second slit portion 121b intersect in a cross shape in a plan view of the main body portion 115. An angle at which the first slit portion 121a and the second slit portion 121b intersect is not particularly limited.

Since the slit constituting the gap 121 is formed at least on the first surface 111, a specific shape and the like of the slit are not limited as long as the medical elongated body 300 can be inserted from the first surface 111 into the main body portion 115 through the slit. For example, the slit constituting the gap 121 may have a linear shape extending from the first surface 111 along the thickness direction of the main body portion 115 at a substantially constant depth. The slit constituting the gap 121 may be different in shapes between the first slit portion 121a and the second slit portion 121b. For example, the first slit portion 121a may be an arc-shaped slit, and the second slit portion 121b may be a linear-shaped slit. When the slit constituting the gap 121 includes a plurality of slit portions such as the first slit portion 121a and the second slit portion 121b, the slit portions 121a and 121b may not be in contact with each other inside the main body portion 115.

An example of the self-repairing material contained in the main body portion 115 includes a self-repairing polymer.

The self-repairing polymer has a function (self-repairing ability) of re-adhering (rebonding) cut surfaces of a polymer sheet when the cut surfaces are brought into contact with each other. Here, the self-repairing polymer is not particularly limited as long as the self-repairing polymer has the above function, and a known polymer can be used. Specifically, for example, a polymer having a bond obtained by an interaction (host-guest interaction) between a host group and a guest group as a crosslinking point as described in JP-A-2017-71710 or WO 2017/159346 can be used. Here, the host group is not limited as long as the host group can include the guest group by the interaction with the guest group. Examples of the host group include a group derived from a compound (host molecule) such as α-cyclodextrin, β-cyclodextrin, γ-cyclodextrin, calix[6]arene sulfonic acid, calix[8] arene sulfonic acid, 12-crown-4, 18-crown-6, [6]paracyclophane, [2,2]paracyclophane, cucurbit[6]uryl, and cucurbit [8]uryl. Among these, from a viewpoint of a self-repairing property (an inclusion property with respect to the guest group) and the like, the host group is preferably a group derived from α-cyclodextrin, a group derived from β-cyclodextrin, or a group derived from γ-cyclodextrin, and more preferably a group derived from γ-cyclodextrin. The guest group is not limited as long as the guest group can be included in the host group by the interaction with the host group. Examples of the guest group include a hydrocarbon group having 4 to 18 carbon atoms such as a butyl group, a hexyl group, a cyclohexyl group, a heptyl group, an octyl group, a nonyl group, a decyl group, an undecyl group, a dodecyl group, a tetradecyl group, a pentadecyl group, a hexadecyl group, a heptadecyl group, an octadecyl group, an adamantyl group, and an isobornyl group, and a substituted hydrocarbon group in which at least one hydrogen atom of the hydrocarbon group is substituted with a hydroxy group, a carboxyl group, an amino group, a halogen atom, an ester group, an amide group, or the like. Among these, from the viewpoint of the self-repairing property (the inclusion property by the host group) and the like, the guest group is preferably a hydrocarbon group having 6 to 12 carbon atoms, preferably an n-butyl group, an n-hexyl group, an n-octyl group, an n-dodecyl group, an adamantyl group, or an isobornyl group, and more preferably an n-octyl group, an n-dodecyl group, an adamantyl group, or an isobornyl group. The host group and the guest group may use one group alone or two or more groups in combination, respectively. Here, a combination of the host group and the guest group is not particularly limited. From the viewpoint of the self-repairing property, the combination of the host group and the guest group (host group-guest group) is preferably (α-cyclodextrin-derived group-n-butyl group), (α-cyclodextrin-derived group-n-hexyl group), (α-cyclodextrin-derived group-n-octyl group), (α-cyclodextrin-derived group-n-dodecyl group), (β-cyclodextrin-derived group-adamantyl group), (β-cyclodextrin-derived group-hydroxyl group substituted adamantyl group), β-cyclodextrin-derived group-ethyl group substituted adamantyl group), β-cyclodextrin-derived group-isobornyl group), (γ-cyclodextrin-derived group-n-octyl group), (γ-cyclodextrin-derived group-n-dodecyl group), and (γ-cyclodextrin-derived group-cyclododecyl group), more preferably (α-cyclodextrin-derived group-n-octyl group), (α-cyclodextrin-derived group-n-dodecyl group), (β-cyclodextrin-derived group-adamantyl group), (β-cyclodextrin-derived group-isobornyl group), (γ-cyclodextrin-derived group-n-octyl group), (γ-cyclodextrin-derived group-n-dodecyl group), and (γ-cyclodextrinderived group-cyclododecyl group), and still more prefer-
ably (γ-cyclodextrin-derived group-n-octyl group),
(γ-cyclodextrin-derived group-n-dodecyl group), and (γ-cy-
clodextrin-derived group-cyclododecyl group).

The self-repairing polymer according to the present
embodiment may be synthesized by a method described in
the above-described publication or the like, or be a com-
mercially available product. Here, examples of the commer-
cially available product include, for example, Wizard® Gel
(registered trademark), Wizard® Pack Heat (Wizard Mono-
mer SMH, Wizard Plus SW), Wizard® Pack Light (Wizard
Monomer SMU, Wizard Plus PKU) (all manufactured by
Yushiro Chemical Industry Co., Ltd.).

An example of the coating layer 125 includes a self-
repairing inhibitor that prevents the inner surface 123 defin-
ing the gap 121 from being coupled by self-repair in a state
in which portions of the inner surface 123 containing the
self-repairing material of the main body portion 115 are in
contact with each other.

The self-repairing inhibitor has an ability of preventing
the self-repairing material from re-adhering (rebonding)
(self-repairing inhibitory ability). Here, the self-repairing
inhibitor is not particularly limited as long as the self-
repairing inhibitor has the above-described function. For
example, a compound containing a guest group correspond-
ing to the guest group in the self-repairing material can be
preferably used. When such a compound is applied to the
inner surface 123 defining the gap 121, the guest group in the
self-repairing inhibitor is included in the host group of the
self-repairing material before the guest group in the self-
repairing material re-interacts with the host group (re-
included in the host group) after the main body portion 115
is cut. Accordingly, the interaction (inclusion) between the
guest group and the host group of the self-repairing material
after the cutting is prevented, and the cut surfaces can be
prevented from re-adhering (rebonding). An example of the
self-repairing inhibitor preferably includes a compound con-
taining the guest group as described above or having a
structure similar in size to the guest group, and more
preferably includes a silicone compound from a viewpoint
of ease of application and the like. The self-repairing inhibi-
tor preferably contains the same group as the guest group in
the self-repairing material. Accordingly, the host-guest inter-
action of the self-repairing material can be more effectively
prevented (the cut surfaces can be more effectively pre-
vented from re-adhering (rebonding)). That is, in a particu-
larly preferred aspect of the present embodiment, the self-
repairing inhibitor is a silicone compound (silicone oil) at
least containing the guest group in the used self-repairing
material or having a structure similar in size to the guest
group. In particular, the silicone compound (silicone oil) is
liquid and has fluidity. Therefore, when the self-repairing
inhibitor is the silicone compound (silicone oil), the coating
layer 125 is maintained on the inner surface 123 defining the
gap 121 accompanying a deformation of the main body
portion 115, and thus it is possible to suitably exert the
ability of preventing the self-repairing material from re-
adhering or re-adhering to itself (rebonding) (self-repairing
inhibitory ability). When the medical elongated body 300 is
inserted into the main body portion 115 through the slit
constituting the gap 121, the coating layer 125 made from
the silicone compound (silicone oil) can also reduce inser-
tion resistance of the medical elongated body 300. Since the
silicone compound (silicone oil) does not require time for
drying and curing in a process of applying the coating layer
125 on the main body portion 115, the coating layer 125 can
be applied on the main body portion 115 with a simple operation. The self-repairing inhibitor may be used alone or
in combination of two or more kinds thereof.

The entire main body portion 115 of the valve body 110
may be implemented by the self-repairing material, or
contain the self-repairing material only in a portion of the
valve body 110 where the first surface 111 is formed. When
a part of the main body portion 115 is implemented by a
material other than the self-repairing material, for example,
silicone rubber, latex rubber, butyl rubber, and isoprene
rubber that are elastic members can be used.

Sheath Introducer 100

As illustrated in FIGS. 1 and 2, the sheath introducer 100
includes the valve body 110, the tubular member 130
including the lumen 131 through which the medical elon-
gated body 300 is insertable, the hub 140 communicating
with the lumen 131 of the tubular member 130, having the
internal space 141 in which the valve body 110 is disposed,
and fixed to the proximal side of the tubular member 130,
and the cap member 150 having a through hole 151 through
which the medical elongated body 300 is insertable and
abutting against the valve body 110 to fix the valve body 110
to the internal space 141 of the hub 140.

The lumen 131 of the tubular member 130 extends
substantially linearly from the proximal side to the distal
side of the tubular member 130. A proximal end of the
tubular member 130 is formed with a proximal end opening
portion that communicates with the internal space 141 of the
hub 140. A distal end of the tubular member 130 is formed
with a distal end opening portion that enables the medical
elongated body 300 to be led out toward the distal side of the
tubular member 130. In the present embodiment, the dilator
main body 210 of the dilator 200 is an example of the
medical elongated body 300.

The hub 140 is connected with a strain relief 160 that
surrounds a predetermined range on the proximal side of the
tubular member 130. The hub 140 is provided with a side
port 142 that communicates with the internal space 141 of
the hub 140. The side port 142 can be connected with one
end portion of a tube 180 (see FIG. 1). The other end portion
of the tube 180 can be connected with, for example, a
three-way stopcock 170.

As illustrated in FIGS. 2 and 7, the valve body 110 is
compressed in a direction (a direction indicated by an arrow
A1 in FIGS. 7 and 8) in which the portions of the inner
surface 123 of the insertion portion 120 that defines the gap
121 come into contact with each other in a state in which the
valve body 110 is fixed to the internal space 141 of the hub
140.

The cap member 150 includes a convex portion 152 that
presses the valve body 110 toward the tubular member 130
(a direction indicated by an arrow B1 in FIGS. 7 and 8).

The cap member 150 is disposed at a proximal end of the
hub 140. The cap member 150 is fitted to the proximal end
of the hub 140 in a manner of surrounding a part of an outer
peripheral surface of the hub 140. The cap member 150 may
have, for example, a structure of being fixed to the hub 140
inside the hub 140. The invention is not limited to fitting,
and the cap member 150 may also be fixed to the hub 140
by, for example, screwing or adhering.

The hub 140 is formed with a step portion 143 that
supports an outer periphery of the valve body 110 and holds
the valve body 110 in the internal space 141. The first
surface 111 of the valve body 110 is disposed on the cap
member 150 side. The second surface 112 of the valve body
110 is disposed on the tubular member 130 side.

As illustrated in FIGS. 2 and 7, a central portion C (a
central portion in the plan view illustrated in FIG. 4) of the valve body 110 exhibits a shape that is recessed toward the tubular member 130 in a state in which the valve body 110 is fixed to the internal space 141 of the hub 140 and is pressed by the convex portion 152. In this state, the first surface 111 of the valve body 110 is compressed in the direction in which the portions of the inner surface 123 of the insertion portion 120 that defines the gap 121 come into contact with each other.

As illustrated in FIGS. 2 and 7, the valve body 110 is compressed in a state of being fixed to the internal space 141 of the hub 140. Portions of the coating layer 125 disposed on the inner surface 123 of the insertion portion 120 that defines the gap 121 come into contact with each other as the valve body 110 is compressed.

An outer peripheral portion of the valve body 110 is sandwiched by the convex portion 152 and the step portion 143. The convex portion 152 is implemented by an end portion of the cap member 150 located on a center of the internal space 141 of the hub 140. The convex portion 152 has a cross-sectional shape inclined toward the tubular member 130. The cross-sectional shape and the like of the convex portion 152 are not particularly limited as long as the convex portion 152 can press the valve body 110 fixed to the internal space 141 of the hub 140 toward the tubular member 130.

Examples of a constituent material from which the tubular member 130 may be fabricated include a polymer material such as polyolefin (for example, polyethylene, polypropylene, polybutene, an ethylene-propylene copolymer, an ethylene-vinyl acetate copolymer, an ionomer, or a mixture of two or more thereof), polyolefin elastomer, crosslinked polyolefin, polyvinyl chloride, polyamide, polyamide elastomer, polyester, polyester elastomer, polyurethane, polyurethane elastomer, fluororesin (for example, polytetrafluoroethylene, or a tetrafluoroethylene-ethylene copolymer), polycarbonate, polystyrene, polyacetal, polyimide, polyetherimide, or polyether ether ketone, or a mixture thereof.

Examples of constituent materials from which the hub 140 and the cap member 150 may be fabricated include polyolefin such as polyethylene or polypropylene, polyamide, polycarbonate, or polystyrene.

Dilator 200

As illustrated FIG. 1, the dilator 200 includes the dilator main body 210 insertable into the lumen 131 of the tubular member 130 of the sheath introducer 100 through the through hole 151 of the cap member 150, and a dilator hub 220 that is fixed to a proximal side of the dilator main body 210.

The dilator 200 can be used to prevent the tubular member 130 from breaking or to widen a perforation on skin when the tubular member 130 of the sheath introducer 100 is inserted into the blood vessel.

When the dilator main body 210 is inserted into the lumen 131 of the tubular member 130, a distal portion of the dilator main body 210 protrudes from the distal end opening portion of the tubular member 130 by a predetermined length.

The distal portion of the dilator main body 210 is formed in a tapered shape tapering toward a distal side. A portion of the dilator main body 210 located closer to the proximal side than the distal portion of the dilator main body 210 extends in the axial direction with a substantially constant outer diameter.

In the present embodiment, a thickness t1 (see FIGS. 3, 5, and 6) of the main body portion of the valve body 110 is smaller than an outer diameter of a maximum outer diameter portion of the dilator main body 210. The maximum outer diameter portion of the dilator main body 210 may be defined by any portion located closer to the proximal side than the distal portion of the dilator main body 210 that has the tapered shape.

Examples of a constituent material from which the dilator main body 210 may be fabricated include a polymer material such as polyolefin (for example, polyethylene, polypropylene, polybutene, an ethylene-propylene copolymer, an ethylene-vinyl acetate copolymer, an ionomer, or a mixture of two or more thereof), polyolefin elastomer, crosslinked polyolefin, polyvinyl chloride, polyamide, polyamide elastomer, polyester, polyester elastomer, polyurethane, polyurethane elastomer, fluororesin (for example, polytetrafluoroethylene, or a tetrafluoroethylene-ethylene copolymer), polycarbonate, polystyrene, polyacetal, polyimide, or polyetherimide, or a mixture thereof.

Examples of a constituent material from which the dilator hub 220 may be fabricated include polyolefin such as polyethylene or polypropylene, polyamide, polycarbonate, or polystyrene.

As illustrated in FIG. 7, when a surgeon inserts the medical elongated body 300 into the lumen 131 of the tubular member 130, the surgeon inserts the medical elongated body 300 into the internal space 141 of the hub 140 through the through hole 151 of the cap member 150. As illustrated in FIG. 8, the surgeon introduces the medical elongated body 300 into the valve body 110 through the through hole 151 of the cap member 150. The valve body 110 is disposed on the hub 140 in a state in which the central portion C of the valve body 110 is concavely curved toward the tubular member 130. Therefore, when the surgeon inserts the medical elongated body 300 into the valve body 110, the surgeon can easily guide the medical elongated body 300 from the first surface 111 to the central portion C of the valve body 110.

When the surgeon brings the medical elongated body 300 into contact with a portion other than the central portion C of the valve body 110, damage such as a laceration may occur in the valve body 110. Even when such damage occurs, the valve body 110 can repair the damage by the self-repairing material contained in the main body portion 115. At least a part of the inner surface 123 of the insertion portion 120 is provided with the coating layer 125 that prevents the gap (slit) 121 from being closed by self-repair. Therefore, the valve body 110 can prevent the gap 121 formed on the first surface 111 from being closed during a period from the time of manufacture until the valve body 110 is used by the surgeon, a period before the valve body 110 is used in a procedure, a period from the time when the medical elongated body 300 is once removed during the procedure until a different medical elongated body 300 is inserted into the valve body 110 again, or the like. Therefore, the surgeon can easily insert the medical elongated body 300 into the valve body 110 through the gap 121 formed on the first surface 111.

As described above, the valve body 110 according to the present embodiment includes the main body portion 115 including the first surface 111, the second surface 112 facing away from the first surface 111, the outer peripheral surface 113 extending between the first surface 111 and the second surface 112, and the insertion portion 120 having the inner surface 123 defining the gap 121 that allows insertion of the medical elongated body 300 and formed at least on the first surface 111. The main body portion 115 contains the self-repairing material that allows self-repairing the damage formed by the contact with the medical elongated body 300. At least a part of the inner surface 123 of the insertion portion 120 is provided with the coating layer 125 that prevents the gap 121 from being closed by self-repair in a state in which the portions of the inner surface 123 of the insertion portion 120 are in contact with each other.

In the valve body 110 configured as described above, since the main body portion 115 of the valve body 110 contains the self-repairing material, even when the damage occurs in the valve body 110 when an operation of inserting the medical elongated body 300 through the gap 121 formed in the valve body 110 is repeated a plurality of times, the damage of the valve body 110 can be repaired by the self-repairing material. Therefore, the valve body 110 can maintain sealing performance of the valve body 110. In the valve body 110, since the inner surface 123 of the insertion portion 120 that defines the gap 121 is provided with the coating layer 125, even in a state in which the portions of the inner surface 123 of the insertion portion 120 are in contact with each other, the gap 121 can be prevented from being closed due to the coupling of the portions of the inner surface 123 by the self-repairing material contained in the valve body 110. Therefore, the valve body 110 allows the surgeon to easily grasp a position of the insertion portion 120 of the valve body 110 based on the gap 121 formed in the valve body 110, and can prevent an increase in the insertion resistance when the surgeon inserts the medical elongated body 300 into the valve body 110.

The gap 121 is a slit formed at least on the first surface 111. The surgeon can smoothly insert the medical elongated body 300 into the valve body 110 through the slit formed on the first surface 111 of the valve body 110.

The slit constituting the gap 121 includes the first slit portion 121*a* extending from the first surface 111 in the thickness direction of the main body portion 115, and the second slit portion 121*b* extending from the second surface 112 in the thickness direction of the main body portion 115. That is, the first slit portion 121*a* extends from the first surface 111 of the main body portion 115 toward the second surface 112 of the main body portion 115, and the second slit portion 121*b* extends from the second surface 112 of the main body portion 115 toward the first surface 111 of the main body portion 115. The first slit portion 121*a* and the second slit portion 121*b* intersect inside the main body portion 115. The coating layer 125 is provided at least on the inner surface 123 defining the first slit portion 121*a*. Since the slit includes the first slit portion 121*a* and the second slit portion 121*b* which intersect inside the main body portion 115, the valve body 110 can reduce the insertion resistance when the medical elongated body 300 is inserted through the valve body 110. In the valve body 110, since the coating layer 125 is provided on the inner surface 123 defining the first slit portion 121*a*, it is possible to suitably prevent the first slit portion 121*a* formed on the first surface 111 from being closed by contact of the portions of the inner surface 123.

The self-repairing material may be a polymer material containing a crosslinking bond which is crosslinked by the interaction between the host group and the guest group. The host group may be γ-cyclodextrin. The guest group may be at least one selected from the group consisting of an adamantyl group and a dodecyl group. Since the self-repairing material contained in the main body portion 115 contains the above material, the valve body 110 can more reliably repair the damage formed in the valve body 110 by the contact with the medical elongated body 300.

The sheath introducer 100 according to the present embodiment includes the valve body 110, the tubular member 130 including the lumen 131 through which the medical elongated body 300 is insertable, the hub 140 communicating with the lumen 131 of the tubular member 130, having the internal space 141 in which the valve body 110 is disposed, and fixed to the proximal side of the tubular member 130, and the cap member 150 having the through hole 151 through which the medical elongated body 300 is insertable and abutting against the valve body 110 to fix the valve body 110 to the internal space 141 of the hub 140. The valve body 110 is compressed in the direction in which the portions of the inner surface 123 of the insertion portion 120 that defines the gap 121 come into contact with each other in a state in which the valve body 110 is fixed to the internal space 141 of the hub 140.

In the sheath introducer 100 configured as described above, in a state in which the valve body 110 is fixed to the internal space 141 of the hub 140, the valve body 110 is compressed in the direction in which the portions of the inner surface 123 of the insertion portion 120 that defines the gap 121 come into contact with each other. In the valve body 110, since at least a part of the inner surface 123 of the insertion portion 120 is provided with the coating layer 125 that prevents the gap 121 from being closed by self-repairing, the gap 121 can be prevented from being closed even in a state in which the valve body 110 is compressed and fixed to the hub 140.

The cap member 150 includes the convex portion 152 that presses the valve body 110 toward the tubular member 130. The central portion C of the valve body 110 is recessed toward the tubular member 130 in a state in which the valve body 110 is fixed to the internal space 141 of the hub 140 and is pressed by the convex portion 152. The first surface 111 of the valve body 110 is compressed in the direction in which the portions of the inner surface 123 of the insertion portion 120 that defines the gap 121 come into contact with each other. In a state in which the valve body 110 is fixed to the internal space 141 of the hub 140, the central portion C of the valve body 110 is concavely curved toward the tubular member 130. Therefore, when the surgeon inserts the medical elongated body 300 into the valve body 110, the surgeon can easily guide the medical elongated body 300 from the first surface 111 to the central portion C of the valve body 110.

The valve body 110 is compressed in a state of being fixed to the internal space 141 of the hub 140. In the valve body 110, the portions of the coating layer 125 disposed on the inner surface 123 of the insertion portion 120 that defines the gap 121 come into contact with each other as the valve body 110 is compressed. Therefore, in a state in which the valve body 110 is fixed to the internal space 141 of the hub 140, the valve body 110 can prevent the portions of the inner surface 123 of the insertion portion 120 from chemically re-adhering (rebonding) while ensuring a physical adhesion state among the portions of the coating layer 125 disposed on the inner surface 123 of the insertion portion 120. Therefore, in the state in which the valve body 110 is fixed to the internal space 141 of the hub 140, the valve body 110 can reliably prevent blood leakage by closing the inner surface 123 of the insertion portion 120 of the valve body 110.

The introducer 10 according to the present embodiment includes the sheath introducer 100 and the dilator 200. The dilator 200 includes the dilator main body 210 insertable into the lumen 131 of the tubular member 130 of the sheath introducer 100 through the through hole 151 of the cap member 150, and the dilator hub 220 that is fixed to the proximal side of the dilator main body 210. The thickness of the main body portion 115 of the valve body 110 is smaller than the diameter of the maximum outer diameter portion of the dilator main body 210. According to the valve body 110 of the present embodiment, the sealing performance of the valve body 110 can be improved by the self-repairing material contained in the main body portion 115. Therefore, even when the thickness of the valve body 110 is small, the sealing performance of the valve body 110 can be maintained satisfactorily. Therefore, the thickness of the valve body 110 can be smaller than the diameter of the maximum outer diameter portion of the dilator main body 210, for example. Accordingly, a size of the valve body 110 can be reduced.

Next, a valve body according to a modification will be described. In the modification, a detailed description about features and aspects of the valve body described above will not be repeated. Features and aspects of the valve body not particularly described in the modification can be the same as those in the embodiment and variations described above.

First Modification

Figures 9, 10:
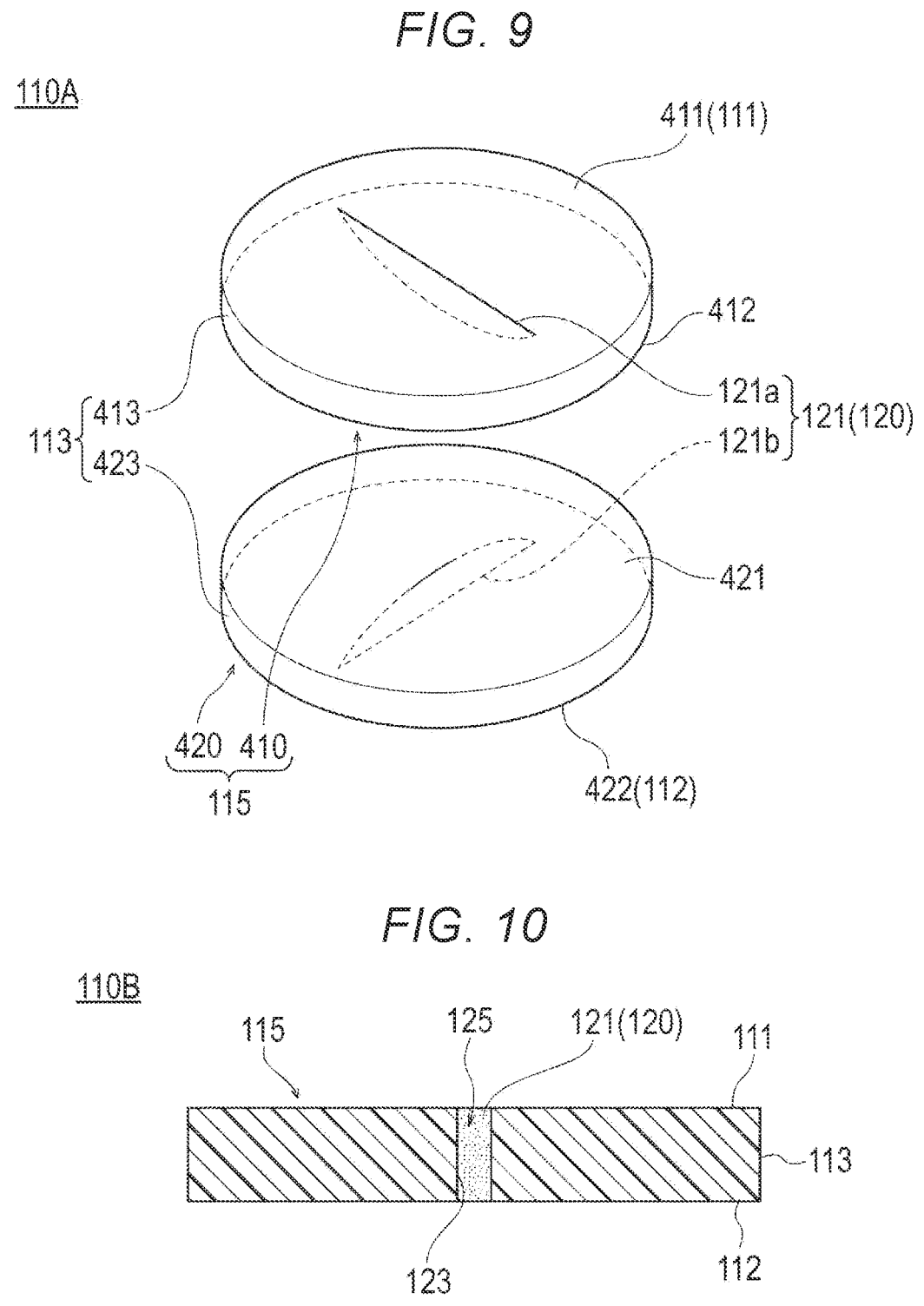

FIG. 9 illustrates a perspective view of a valve body 110A according to a first modification.

The valve body 110A may include, for example, two main body portions including a first main body portion 410 and a second main body portion 420.

The first main body portion 410 includes a first surface 411, a second surface 412, and an outer peripheral surface 413 extending between the first surface 411 and the second surface 412.

The second main body portion 420 includes a first surface 421, a second surface 422, and an outer peripheral surface 423 extending between the first surface 421 and the second surface 422.

The first main body portion 410 and the second main body portion 420 may overlap each other in the internal space 141 of the hub 140. The second surface 412 of the first main body portion 410 may face the first surface 421 of the second main body portion 420 in the internal space 141 of the hub 140. The main body portion 115 of the valve body 110A may include the two main body portions 410 and 420 disposed in this manner. The first surface 411 of the first main body portion 410 constitutes the first surface 111 of the main body portion 115. The second surface 422 of the second main body portion 420 constitutes the second surface 112 of the main body portion 115. The outer peripheral surface 113 of the main body portion 115 includes the outer peripheral surface 413 of the first main body portion 410 and the outer peripheral surface 423 of the second main body portion 420 overlapping each other.

The first surface 411 of the first main body portion 410 is formed with the first slit portion 121a extending in a thickness direction of the first main body portion 410. The first slit portion 121a extends from the first surface 411 by a length (depth) reaching the second surface 412. The second surface 422 of the second main body portion 420 is formed with the second slit portion 121b extending in a thickness direction of the second main body portion 420. The second slit portion 121b extends from the second surface 422 by a length (depth) reaching the first surface 421. The slit portions 121a and 121b collectively define a slit constituting the gap 121.

In the valve body 110A according to the first modification, similar to the valve body 110 described above, a coating layer that prevents the gap 121 from being closed by a self-repairing material is provided on at least a part of an inner surface of the insertion portion 120 of the valve body 110A. Therefore, the valve body 110A allows a surgeon to easily grasp a position of the insertion portion 120 of the valve body 110A based on the gap 121 formed in the valve body 110A, and can prevent an increase in insertion resistance when the surgeon inserts the medical elongated body 300 into the valve body 110A.

Second Modification

FIG. 10 illustrates a cross-sectional view of a valve body 1106 according to a second modification.

In the valve body 1106 according to the second modification, the gap 121 is implemented by a hole. The hole constituting or defining the gap 121 penetrates or passes through the main body portion 115 along a thickness direction of the main body portion 115 of the valve body 1106 so that the hole defines a through gap passing completely through the main body portion 115. The inner surface 123 of the insertion portion 120 that defines the hole is provided with the coating layer 125. As illustrated in the present modification, a specific structure of the gap 121 is not particularly limited as long as the medical elongated body 300 can be inserted into the main body portion 115 of the valve body 1106.

In a state in which the valve body 1108 is fixed to the internal space 141 (see FIG. 2) of the hub 140, the hole constituting the gap 121 is compressed toward a central portion C of the valve body 1108, and the portions of the inner surface 123 defining the hole come into contact with each other. The coating layer 125 provided on the inner surface 123 can prevent the hole from being closed due to connection of the inner surface 123 defining the hole as a result of the aforementioned contact.

Other Modifications

A valve body according to the disclosure here may be formed with an insertion portion having an inner surface that defines a gap (for example, a slit or a hole) formed at least on a part of a first surface of the valve body (a surface disposed on the cap member 150 side when applied to the sheath introducer 100). Therefore, the gap may not be formed over an entire thickness direction of the valve body. However, from a viewpoint of preventing a remarkable decrease in insertability of the medical elongated body 300 into the valve body, it is preferable that the gap has a length equal to or more than half a thickness of a main body portion from the first surface.

Other Embodiments

Next, a connector member according to another embodiment will be described. In the present embodiment, features and aspects of the connector member that have already been described will not be repeated. Features and aspects of the connector member not particularly described in the present embodiment can be the same as those in the embodiment and the modifications described above.

Figure 11:
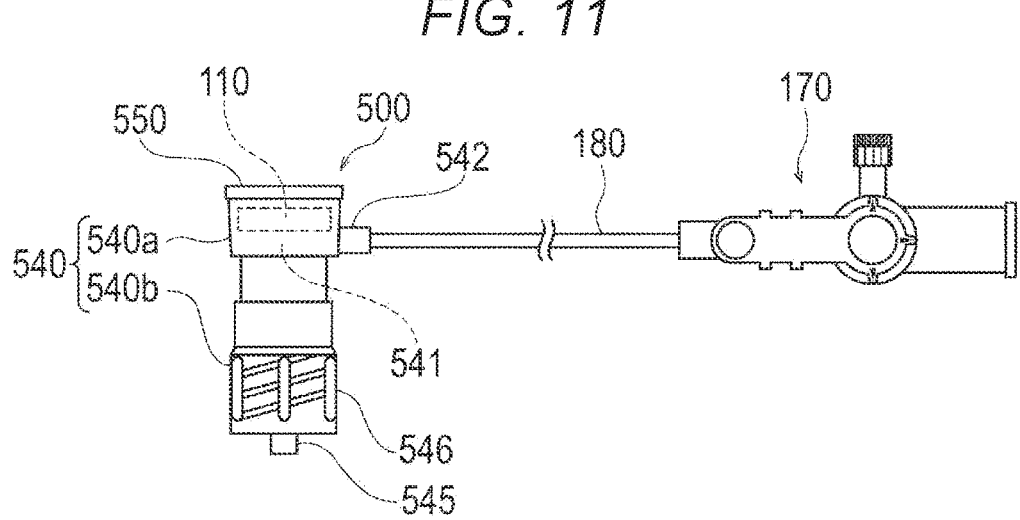
FIG. 11 is a view illustrating a connector member according to another embodiment.

FIG. 11 illustrates a connector member 500 including the valve body 110. The connector member 500 can be used, for example, by being connected to a catheter (for example, a guiding catheter) including a hub in which the valve body 110 is not disposed. By connecting the connector member 500 to the hub disposed at a proximal portion of the catheter, an air inflow into the catheter can be prevented and blood leakage from a proximal end of the catheter can be reduced in a state in which a medical elongated body (a guide wire, another catheter device, or the like) used in combination with the catheter is inserted into the valve body 110. A specific structure, type, and the like of the catheter to which the connector member 500 is applied are not particularly limited.

The connector member 500 includes a hub 540. The hub 540 includes a main body portion 540a and a connector portion 540b.

The main body portion 540a has an internal space 541 in which the valve body 110 is disposed. The internal space 541 is provided with a step portion that holds the valve body 110. A cap member 550 that holds the valve body 110 in the internal space 541 is attached to the hub 540. A cross-sectional shape and a structure of the internal space 541 of the hub 540 of the connector member 500, a cross-sectional shape and a structure of the cap member 550, and the like can be the same as, for example, those of the hub 140 and the cap member 150 (see FIG. 2) of the sheath introducer 100 according to the embodiment described above.

The main body portion 540a is provided with a side port 542 that communicates with the internal space 541. The side port 542 may be connected with one end portion of the tube 180. The other end portion of the tube 180 may be connected with, for example, the three-way stopcock 170. The connector member 500 may not include the tube 180 or the three-way stopcock 170.

The connector portion 540b includes a male connector portion 545 convexly protruding from the main body portion 540a, and a screw adapter portion 546 rotatably held by the male connector portion 545. The screw adaptor portion 546 is connected to the male connector portion 545 in a state of being prevented from coming off. The screw adapter portion 546 can move by a predetermined distance along an axial direction in which the male connector portion 545 extends. A surgeon can fix the connector member 500 to the hub of the catheter by moving the screw adapter portion 546 in the axial direction while rotating the screw adapter portion 546 in a state in which the male connector portion 545 is inserted into the hub of the catheter. A specific configuration for fixing the connector member 500 to the hub of the catheter is not particularly limited.

In the connector member 500 according to the present embodiment, since the inner surface 123 defining the gap 121 in the insertion portion 120 of the valve body 110 is provided with the coating layer 125, even in a state in which portions of the inner surface 123 of the insertion portion 120 are in contact with each other, the gap 121 can be prevented from being closed due to connection of the portions of the inner surface 123 by the self-repairing material contained in the valve body 110. Therefore, the valve body 110 allows the surgeon to easily grasp a position of the insertion portion 120 of the valve body 110 based on the gap 121 formed in the valve body 110, and can prevent an increase in insertion resistance when the surgeon inserts the medical elongated body into the valve body 110. By connecting the connector member 500 to the catheter that does not include the valve body 110, the surgeon can prevent the air inflow into the catheter and can reduce the blood leakage from the proximal end of the catheter when using the catheter.

Although the valve body, the sheath introducer, and the connector member have been described above through the embodiments, variations and modifications, the invention is not limited only to the configurations described above, and can be appropriately changed based on the description of the claims.

The structure of each part, the arrangement of members, and the like described in the specification can be appropriately changed, and it is possible to omit the use of additional members described with reference to the drawings, and to use other additional members and the like appropriately. The detailed description above describes embodiments, variations and modifications of the valve body, sheath introducer and connector member representing examples of the new valve body, sheath introducer and connector member disclosed here. The invention is not limited, however, to the precise embodiments, variations and modifications described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An introducer comprising:

a sheath introducer to allow an elongated medical body to be introduced into a blood vessel, the sheath introducer comprising:

a tubular member including a lumen through which the elongated medical body is insertable, the tubular member including a proximal end;

a hub connected to the proximal end of the tubular member and including an internal space in communication with the lumen of the tubular member;

a valve body positioned in the internal space of the hub;

a cap member abutting against the valve body to fix the valve body in the internal space of the hub, the cap member including a through hole through which the elongated medical body is insertable;

the valve body comprising: a main body portion that includes oppositely facing first and second surfaces, and an outer peripheral surface extending between the first surface and the second surface, the main body portion possessing a thickness; an insertion portion having a gap that allows insertion of the elongated medical body, the gap intersecting the first surface of the main body portion and extending from the first surface of the main body portion towards the second surface of the main body portion, the main body portion including inner surface portions that face the gap and face toward each another; the main body portion containing a self-repairing polymer material that allows re-adhering of cut portions of the main body portion that are cut as a result of contact with the elongated medical body to thereby self-repair damage of the main body portion; and at least parts of the inner surface portions are in contact with each other and are provided with a coating layer that prevents the gap from being closed by the self-repairing material when the parts of the inner surface portions face one another and are in contact with each other; and a dilator comprising:

a dilator main body insertable into the lumen of the tubular member of the sheath introducer through the through hole of the cap member, the dilator main body having a proximal end and a maximum outer diameter portion at which an outer diameter of the dilator main body is a maximum outer diameter of the dilator main body;

a dilator hub fixed to the proximal end of the dilator main body; and a thickness of the main body portion of the valve body being smaller than the outer diameter of the maximum outer diameter portion of the dilator main body.

2. The dilator according to claim 1, wherein the dilator main body possesses a length such that when the dilator main body is inserted into the lumen of the tubular member of the sheath introducer through the through hole of the cap member, a distal end portion of the dilator main body projects distally beyond a distal end of the tubular member of the sheath introducer so that the distal end portion of the dilator main body is positioned outside the tubular member of the sheath introducer.

3. A sheath introducer configured to allow an elongated medical body to be introduced into a blood vessel, the sheath introducer comprising:

a tubular member including a lumen through which the elongated medical body is insertable, the tubular member including a proximal end;

a hub connected to the proximal end of the tubular member and including an internal space in communication with the lumen of the tubular member;

a valve body positioned in the internal space of the hub; and a cap member abutting against the valve body to fix the valve body in the internal space of the hub, the cap member including a through hole through which the elongated medical body is insertable;

the valve body comprising: a main body portion that includes oppositely facing first and second surfaces, and an outer peripheral surface extending between the first surface and the second surface; an insertion portion having a gap that allows insertion of the elongated medical body, the gap intersecting the first surface of the main body portion and extending from the first surface of the main body portion towards the second surface of the main body portion, the main body portion including inner surface portions that face the gap and face toward each another; the main body portion containing a self-repairing material that allows self-repair of damage of the main body portion, formed by contact with the elongated medical body;

the valve body being positioned in the internal space of the hub and being compressed by the cap member in a direction causing the inner surface portions to contact each other; and and at least parts of the inner surface portions that are in contact with each other being provided with a coating layer that prevents the gap from being closed by the self-repairing material when the inner surface portions are in contact with each other.

4. The sheath introducer according to claim 3, wherein the gap is a slit or a hole.

5. The sheath introducer according to claim 3, wherein the gap is a slit that comprises a first slit portion and a second slit portion, the inner surface portions being first inner surface portions positioned on opposite sides of the first slit portion, the main body portion including second inner surface portions that face one another and are positioned on opposite sides of the second slit portion, the first slit portion terminating in a thickness direction of the main body portion at a position spaced from the second surface of the main body portion, the second slit portion extending from the second surface of the main body portion toward the first surface of the main body portion, the second slit portion terminating in a thickness direction of the main body portion at a position spaced from the first surface of the main body portion, the coating layer being provided at least on the first inner surface portions that are positioned on opposite sides of the first slit portion.

6. The sheath introducer according to claim 5, wherein the coating layer is additionally provided at least on a part of the second inner surface portions.

7. The sheath introducer according to claim 5, wherein at least one of the first slit portion and the second slit portion is an arc-shaped slit portion.

8. The sheath introducer according to claim 3, wherein the gap is a slit that comprises a first slit portion and a second slit portion, the inner surface portions being first inner surface portions positioned on opposite sides of the first slit portion, the main body portion including second inner surface portions that face one another and are positioned on opposite sides of the second slit portion, the first slit portion terminating in a thickness direction of the main body portion at a position spaced from the second surface of the main body portion, the second slit portion extending from the second surface of the main body portion toward the first surface of the main body portion, the second slit portion terminating in a thickness direction of the main body portion at a position spaced from the first surface of the main body portion, the first slit portion and the second slit portion intersecting each other as seen in a plan view of the main body portion.

9. The sheath introducer according to claim 3, wherein the self-repairing material is a polymer material containing a crosslinking bond crosslinked by an interaction between a host group and a guest group, the host group being γ-cyclo-dextrin, and the guest group being at least one selected from the group consisting of an adamantyl group and a dodecyl group.

10. The sheath introducer according to claim 3, wherein:

the cap member includes a convex portion that presses the valve body toward the tubular member;

a central portion of the valve body is recessed toward the tubular member; and the first surface of the valve body is compressed by the convex portion of the cap member to cause the parts of the inner surface portions to contact each other.

11. The sheath introducer according to claim 10, wherein the valve body is compressed so that portions of the coating layer disposed on the inner surface portions come into contact with each other.

12. A valve body positionable in an internal space of a medical device hub and configured to permit an elongated medical body to be inserted into and pass through the valve body while also preventing fluid flow through the valve body before insertion of the elongated medical body into the valve body, the valve body comprising:

a main body portion including a first surface, a second surface facing away from the first surface, an outer peripheral surface extending between the first surface and the second surface, and an insertion portion having a gap that allows insertion of the elongated medical body, the gap intersecting the first surface of the main body portion and extending from the first surface of the main body portion towards the second surface of the main body portion, the main body portion including inner surface portions that face the gap and that are in contact with each other, the main body portion containing a self-repairing material that allows self-repair of damage of the main body portion resulting from contact with the elongated medical body, and and at least parts of the inner surface portions that are in contact with each other being provided with a coating layer that prevents the gap from being closed by the self-repairing material when the parts of the inner surface portions of the insertion portion face the gap and are in contact with each other.

13. The valve body according to claim 12, wherein the gap is a slit or a hole.

14. The valve body according to claim 12, wherein the gap is a slit that includes a first slit portion extending from the first surface of the main body portion in a thickness direction of the main body portion, and a second slit portion extending from the second surface of the main body portion in the thickness direction of the main body portion, the first slit portion and the second slit portion intersect each other inside the main body portion, the inner surface portions are positioned on opposite sides of the first slit portion, and the coating layer is provided at least on parts of the inner surface portions that are positioned on opposite sides of the first slit portion.

15. The valve body according to claim 12, wherein the self-repairing material is a polymer material containing a crosslinking bond crosslinked by an interaction between a host group and a guest group, the host group being γ-cyclo-dextrin, and the guest group being at least one selected from the group consisting of an adamantyl group and a dodecyl group.

16. The valve body according to claim 12, wherein the gap is a slit that comprises a first slit portion and a second slit portion, the first slit portion extending from the first surface of the main body portion toward the second surface of the main body portion, the first slit portion terminating in a thickness direction of the main body portion at a position spaced from the second surface of the main body portion, the second slit portion extending from the second surface of the main body portion toward the first surface of the main body portion, the second slit portion terminating in a thickness direction of the main body portion at a position spaced from the first surface of the main body portion, the inner surface portions being first inner surface portions positioned on opposite sides of the first slit portion, the main body portion including second inner surface portions that face one another and are positioned on opposite sides of the second slit portion, wherein the parts of the inner surface portions that are provided with the coating layer are positioned on opposite sides of the first slit portion.

17. The valve body according to claim 16, wherein the coating layer is additionally provided at least on a part of the second inner surface portions.

18. The valve body according to claim 16, wherein at least one of the first slit portion and the second slit portion is an arc-shaped slit portion.

19. The valve body according to claim 12, wherein the gap is a slit that comprises a first slit portion and a second slit portion, the first slit portion extending from the first surface of the main body portion toward the second surface of the main body portion, the first slit portion terminating in a thickness direction of the main body portion at a position spaced from the second surface of the main body portion, the second slit portion extending from the second surface of the main body portion toward the first surface of the main body portion, the second slit portion terminating in a thickness direction of the main body portion at a position spaced from the first surface of the main body portion, the first slit portion and the second slit portion crossing each other as seen in a plan view of the main body portion.

20. The valve body according to claim 12, wherein the gap is a through gap passing completely through the main body portion so that the through gap communicates with both the first surface of the main body portion and the second surface of the main body portion, the inner surface portions facing the through gap and being covered by the coating layer.

* * * * *